(12) United States Patent
Hull et al.

(10) Patent No.: US 11,776,667 B2
(45) Date of Patent: Oct. 3, 2023

(54) COMPOSITION TRACKING OF MIXED SPECIES IN CHEMICAL PROCESSES

(71) Applicant: Bryan Research & Engineering, LLC, Bryan, TX (US)

(72) Inventors: Ashley Hull, Bryan, TX (US); Kevin Lunsford, Bryan, TX (US)

(73) Assignee: Bryan Research & Engineering, Bryan, TX (US)

( * ) Notice: Subject to any disclaimer, the term of this patent is extended or adjusted under 35 U.S.C. 154(b) by 985 days.

(21) Appl. No.: 16/692,085

(22) Filed: Nov. 22, 2019

(65) Prior Publication Data

US 2021/0089689 A1    Mar. 25, 2021

Related U.S. Application Data

(60) Provisional application No. 62/904,806, filed on Sep. 24, 2019.

(51) Int. Cl.

| | |
|---|---|
| *G01N 33/48* | (2006.01) |
| *G01N 33/50* | (2006.01) |
| *G16C 20/90* | (2019.01) |
| *G16C 20/10* | (2019.01) |
| *G16C 20/30* | (2019.01) |
| *G06F 111/10* | (2020.01) |

(52) U.S. Cl.
CPC ............. *G16C 20/90* (2019.02); *G16C 20/10* (2019.02); *G16C 20/30* (2019.02); *G06F 2111/10* (2020.01)

(58) Field of Classification Search
CPC ......... G16C 20/90; G16C 20/10; G16C 20/30
See application file for complete search history.

(56) References Cited

U.S. PATENT DOCUMENTS

2015/0157752 A1*   6/2015   Varshney ............ A23L 3/34095
                                                                73/23.34

OTHER PUBLICATIONS

Myers et al. Thermodynamics of mixed-gas adsorption. AIChE Journal, vol. 11, pp. 121-127. (Year: 1965).*

* cited by examiner

*Primary Examiner* — Russell S Negin
(74) *Attorney, Agent, or Firm* — Craige Thompson; Thompson Patent Law; Timothy D. Snowden

(57) ABSTRACT

Systems and methods of chemical process simulation providing improved methods and systems for expressing the composition of a stream in a chemical process model in a manner that is not immediately indicative of the underlying composition, providing for improved accuracy of allocation of a process output stream to the appropriate source(s), avoiding duplication of components or other inaccurate component representations in relation to critical calculations, and improving the operation of a computer or other computing system for performing chemical process modeling and simulation. The systems or methods provide for three distinct layers of interaction, separating mixed species displayed to the user from individual species used in calculations, while providing transformation objects between dataset layers to provide for accurate modeling, calculation, and display.

20 Claims, 6 Drawing Sheets

| | MOLAR FLOW lbmol/h | MOLE FRACTION % | MASS FLOW lb/h | MASS FRACTION % | STD VAPOR VOLUMETRIC FLOW MMSCFD | NORMAL VAPOR VOLUMETRIC FLOW MMCFD | STD LIQUID VOLUMETRIC FLOW sgpm | STD LIQUID VOLUMETRIC FRACTION % |
|---|---|---|---|---|---|---|---|---|
| Carbon Dioxide | 0.193018 | 0.00916701 | 8.49461 | 0.0138433 | 0.00175793 | 0.00166321 | 0.0207807 | 0.0173172 |
| Hydrogen Sulfide | 0.0204438 | 0.000970939 | 0.696742 | 0.00113545 | 0.000186194 | 0.000176162 | 0.00174355 | 0.00145295 |
| Methane | 0 | 0 | 0 | 0 | 0 | 0 | 0 | 0 |
| Ethane | 0 | 0 | 0 | 0 | 0 | 0 | 0 | 0 |
| Propane | 0 | 0 | 0 | 0 | 0 | 0 | 0 | 0 |
| n-Butane | 0 | 0 | 0 | 0 | 0 | 0 | 0 | 0 |
| n-Pentane | 0 | 0 | 0 | 0 | 0 | 0 | 0 | 0 |
| n-Hexane | 0 | 0 | 0 | 0 | 0 | 0 | 0 | 0 |
| MDEA | 0 | 0 | 0 | 0 | 0 | 0 | 0 | 0 |
| DEA | 0 | 0 | 0 | 0 | 0 | 0 | 0 | 0 |
| Water | 1872.87 | 88.9487 | 33740.4 | 54.985 | 17.0574 | 16.1384 | 67.4494 | 56.2078 |
| Proprietary Solvent | 232.479 | 11.0412 | 27613.3 | 45 | 2.11733 | 2.00325 | 52.5281 | 43.7734 |

COMPOSITION TRACKING OF MIXED SPECIES IN CHEMICAL PROCESSES

CROSS-REFERENCE TO RELATED APPLICATION

This application claims priority to provisional application 62/904,806, filed Sep. 24, 2019. The contents and disclosures of each of these applications are incorporated herein by reference in their entirety for all purposes.

FEDERALLY SPONSORED RESEARCH

Not Applicable

SEQUENCE LISTING

Not Applicable

BACKGROUND OF THE INVENTION

Chemical process modeling is the representation of the physical and chemical operations on materials via mathematical modeling. One of the most important representations is the composition of a stream or unit of material. For the sake of simplicity or secrecy it is often convenient to express the composition of a stream in a chemical process model in a manner that is not immediately indicative of the underlying composition.

FIELD OF THE INVENTION

This invention relates to the field of chemical processes. Specifically, it relates to composition tracking in chemical process design, analysis, monitoring, reporting, and the like. In some embodiments, the invention particularly relates to oil and gas process modeling, including design, analysis, monitoring, and reporting.

DESCRIPTION OF THE RELATED ART

Various approaches have been used to track compositions in chemical process models:

Over-Simplified Components:

A blended component could be represented by a fiction that it is the average of the properties of the mixture. An example of this would be the pseudo-components frequently used in oil processing. A simple crude oil may be made up of millions of distinct components. Due to the difficulty in analyzing and accounting for this number of molecules, oils are often described by 'cuts' or groups of molecules of similar boiling temperature. However, a pseudo-component often does not properly represent the properties of the true underlying mixture, especially if the underlying mixture represents a wide range of properties such as boiling point, molecular weight or reactivity. In some cases, air can be represented by an average of its constituent parts. However, if the capacity for combustion is required, the simulation must maintain the underlying oxygen content.

Duplication:

One approach to the oil/natural gas source accounting problem is to create a composition profile made up of components unique to the source. For example, suppose there were three natural gas wells 'A', 'B', and 'C' that each produced some methane, ethane, and propane. A model could be configured to have nine components: A-methane, A-ethane, A-propane, B-methane, B-ethane, B-propane, C-methane, C-ethane, and C-propane. This allows the explicit accounting for how much of each molecule came from each source.

As one might observe, for a case with many sources and many components, the composition vector can grow unreasonably and intractably large. The calculation time required for many chemical process calculations is on the order of $N^2$, where N is the number of components. Thus, calculation time quickly reaches extremely long times that render modeling practically unusable.

In addition, there are important chemical process calculations that depend on logarithmic functions, and potentially other duplicated-component-sensitive functions. By maintaining three separate versions of the component methane (duplicated components), this calculation is done improperly. For example, performing compressor calculations and entropy calculations, among others, with duplicated components introduces errors. As calculations are performed through the chemical process, errors are potentially amplified. Example errors are provided in Table 2.

Finally, viewing the aggregate of any source or any underlying component requires the user to manipulate or process the composition in an additional step, increasing the tediousness and decreasing the usefulness of modeling.

Single Source

Single-source modeling is a technique for calculating the oil well allocation problem. The user enters the data for each of the sources one at a time and runs the model. The single source solution is a crude approximation for the multiple source problem. However, phase equilibrium behavior is strongly influenced by the composition. If the source compositions differ significantly, the phase separation will be inaccurate. In addition, the efficiency of many operations is dependent on the flow. For example, the efficiency of a compressor may be much different simulating one flow as compared to a fraction of that flow.

Difference

Difference modeling is another technique for approaching the oil well allocation problem. At first, the full flow of all sources is simulated. Then, one at a time, the sources are removed. The difference in product flows are attributed to the removed source, and the difference in production is allocated to the removed source. While this more closely approaches the allocation of the full flow, it still does not exactly represent the fraction of production related to each source.

Proprietary Compositions

Furthermore, some chemical process simulation software packages provide for use of proprietary compositions, such as proprietary solvents, and for preserving the secrecy of the composition thereof. However, such packages only provide for use of a single proprietary composition at one time, and do not provide for simulating the use of multiple compositions simultaneously. A non-exhaustive list of potential errors are provided in Table 2.

Conclusion

What is needed is a system that allows a user to model and design, analyze, monitor, report, and the like, chemical processes using accurate compositions, and keep track of component sources, while minimizing repetitive work and preventing duplication of components, in order to create accurate and efficient models that are useful and not prohibitively tedious or time-consuming to setup or run.

BRIEF SUMMARY OF THE INVENTION

The present invention provides systems and methods for chemical process simulation. In particular, it provides improved methods and systems for expressing the composition of a stream I in a chemical process model in a manner that is not immediately indicative of the underlying composition, provides for improved accuracy of allocation of a process output stream to the appropriate source(s), avoids duplication of components or other inaccurate component representations in relation to critical calculations, and improves the operation of a computer or other computing system for performing chemical process modeling and simulation. The systems or methods provide for distinct layers of interaction, separating the chemical species displayed to the user from chemical components used in calculations, while providing mapping between dataset layers to provide for accurate modeling, calculation, and display.

BRIEF DESCRIPTION OF THE DRAWINGS

Various embodiments of the present embodiments are described with reference to the following FIGURES Like reference numerals therein refer to like parts throughout the various views unless otherwise specified. Embodiments and portions of embodiments illustrated and described herein are non-limiting and non-exhaustive.

FIG. 1A and FIG. 1B together making up the entire chemical process schematic.

FIG. 6B is an example GUI portion.

DETAILED DESCRIPTION OF THE INVENTION

Figure 1A:
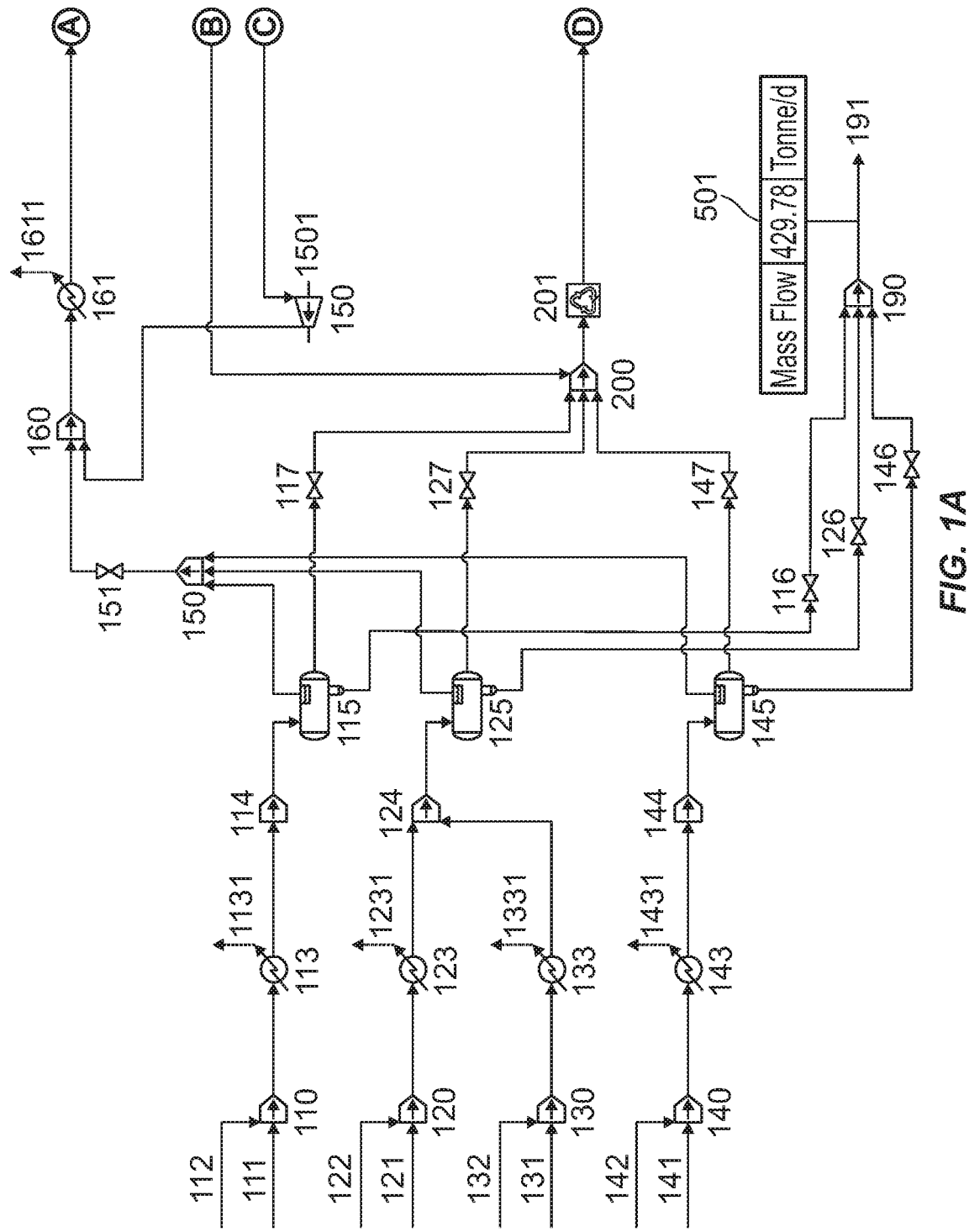
FIG. 1A is a schematic process model of one portion of an example chemical process.

The following description of various embodiments of the invention, combined with the associated drawings, enables persons of ordinary skill in the art to both practice the preferred embodiments of the invention, and to understand related applications and embodiments of the invention that may not be specifically set forth, but are encompassed by the specification and claims.

General Embodiment

Embodiments disclosed herein relate to composition tracking in chemical process design, analysis, monitoring, reporting, and the like. In some embodiments, the invention particularly relates to oil and gas process modeling, including design, analysis, monitoring, and reporting. In particular, various embodiments disclosed herein provide specific implementations of solutions to at least the problems in the software arts discussed above, and provide improved systems, methods, and combinations thereof for managing composition data, thereby providing specific improvement to computer functionality.

In general, the embodiments are intended to operate as, or in the context of, computer code in a computer system. A computer system, in various embodiments, comprises a single personal computer, one or more distributed computing networks, one or more servers and fat clients or thin clients or both, other known computer systems, or various combinations thereof. In general, a computer system comprises at least one data processing unit, and at least one data storage device. The data storage device(s) generally stores computer code, and stored input and output from the computer code, and the data processing unit(s) executes computer code to process user and software input and output.

System

In some embodiments of the invention, the embodiments relate to a system for modeling of chemical processes comprising:

(1) a computer system comprising a data processing unit, and having access to at least one data storage device; and (2) computer code in said computer system, said computer code comprising:

(a) a means for creating, reading, or both, chemical process diagrams; each process comprising one or more unit operations, one or more input streams into each unit operation, and one or more output streams from each unit operation; each of the streams comprising chemical composition data; each of the unit operations comprising one or more calculations transforming data from at least one of the streams connected thereto and accordingly updating data of at least one of the streams connected thereto;

(b) three layers: an external layer, a middle layer, and an internal layer; the external layer comprises mixed species, individual species, or both, as determined by a user; the middle layer comprises individual species duplicated by source; and the internal layer comprises only unique individual species;

(c) transformation objects to convert between the three layers;

(d) component-sensitive calculation rules directing each unit operation, or portion thereof, to operate on either the middle layer or internal layer; and (e) calculation efficiency rules directing each unit operation, or portion thereof, to operate on either the middle layer or internal layer.

Method

In some embodiments of the invention, the embodiments relate to a method for improving the operation of at least one computer during chemical process modeling, the method comprising:

(a) evaluating a chemical process model; the process model comprising one or more unit operations, one or more input streams into each unit operation, and one or more output streams from each unit operation; each of the streams comprising chemical composition data; each of the unit operations comprising one or more calculations transforming data from at least one of the streams connected thereto and accordingly updating data of at least one of the streams connected thereto;

(b) maintaining stream composition data in three layers: an external layer, a middle layer, and an internal layer; the external layer comprises mixed species, individual species, or both, as determined by a user; the middle layer comprises individual species duplicated by source; and the internal layer comprises only unique individual species;

(c) applying component-sensitive calculation rules to direct each unit operation, or portion thereof, to operate on either the middle layer or internal layer;

(d) applying calculation efficiency rules directing each unit operation, or portion thereof, to operate on either the middle layer or internal layer; and (e) applying transformation objects to convert between the three layers as directed by rules, including the component-sensitive calculation rules and the calculation efficiency rules.

(f) Computer Readable Medium

In some embodiments of the invention, the embodiments relate to at least one non-transient computer readable medium containing program instructions for causing a computer to perform a method for improving the operation of at least one computer during chemical process modeling, the method comprising the method discussed above.

Core Components

Embodiments of the invention comprise the following core components. Various combinations of the different elements of embodiments of the invention as herein defined will be obvious to those skilled in the art as appropriate for the specific application and environment of use. Example processes and calculations benefiting from the improved system and methods of composition tracking presented herein, having at least three layers, are presented in Table 1.

Specific examples and embodiments of this method and related apparatus will serve to illustrate to persons skilled in the art the broader concepts disclosed.

Mixed Species

The present invention provides for the creation of composite components known as "mixed species." A mixed specie is created from "native" or "real" species (components), or components of known properties and suitable for use in process modeling (e.g. pentane, methane, nitrogen, oxygen, piperazine, MDEA, etc.) or components used to approximate a mixture of components (e.g., an oil cut that represents a range of real components that have similar boiling points, a component such as one named C6+ that represents all components with a higher molecular weight than pentane, etc.) The blend of any given mixed specie is defined by at least one of the user or the system.

As used herein, "mixed specie," the singular form, refers to a specific group of real species, for example the "mixed specie" denominated "air," would comprise the individual native species of nitrogen, oxygen, etc. "Mixed species," the plural form, refers to the concept of representing a combination of individual species as a single entity, or to multiple such combinations (more than one mixed specie).

A mixed specie is a mixture, although in various embodiments, an individual specie maybe named and entered like a mixed specie. Physically, a mixed specie is a mixture, and is made up of two or more physically combined substances. In various embodiments a mixed specie: can represent a commonly known blend of components, such as air (comprising components such as O2 and N2); can represent a proprietary blend which, in some embodiments, comprises both common and user-known components; can represent a mixture from a specified source, such as an oil well; or any suitable combinations thereof or other suitable chemical arrangements. Rules are provided that allow the mixed specie and components to be manipulated by user and software in three layers: external, middle, and internal. Mixtures include suspensions, solutions, emulsions, alloys, etc.

In preferred embodiments, a mixed specie is uni-dimensional, in other words, it is not made up of other mixed species. Various manufacturers provide proprietary mixed species that are used in chemical processes modeled in various embodiments herein.

External Layer

The "external layer," also referred to as the "top layer" or "user interaction layer," receives data from the user, reports data to the user, or both, in at least one preferred composition profile. This preferred composition profile necessarily includes the named mixed specie(s).

Implied component duplicates are allowed in this layer, but duplicates are not displayed as such. For example, if Air is included as a mixed specie, comprising N2, and Proprietary Gas A is included as a mixed specie, also comprising N2, N2 is an implied duplicate component; however, it is not displayed as a duplicated component: it simply is part of the non-duplicated composition. In other words, the external layer simply shows Air and Proprietary Gas A, and does not show N2-Proprietary Gas A, N2-Air, etc.

In preferred embodiments, the user interacts solely with the external layer, which is why it is also referred to as the "user interaction layer." Although in most embodiments the user may view some or all of the middle and internal layers, the user may only interact with—or enter data directly into—the external layer. In such embodiments, the user selects, defines, or both, the mixed species, individual species, or both, as appropriate, for each input stream. This data is in the external layer, and is attached to the appropriate input stream(s). For each input stream, the user provides sufficient data to determine the proportion of each component in each input stream.

For example, if an input stream comprises Mixed Specie (MS)-A and MS-B, and the components of MS-A are pre-defined, but MS-B is a custom mixed specie, than the user creates the input stream, and selects MS-A, and creates MS-B, inputting each component of MS-B. Further, the user indicates the amount of MS-A, and of MS-B, and the proportion of each component of MS-B to the total of MS-B, as a percentage, ratio, mass fraction, mole fraction, etc. In preferred embodiments, the user sets the flow rate of the input stream. From this data, the modeling software is able to apply pre-defined rules and equations to transform the external layer to the source-specific components of the middle layer, and the unique components of the internal layer, as required. In various embodiments, the user pre-defines one or more custom mixed species prior to creating an input stream, and then simply selects the custom mixed specie. In some embodiments, the user may pre-define custom mixed species or may enter it 'on-the-fly' while creating or editing a stream, etc.

Alternatively, if appropriate, the user can add two input streams: I Stream 1 comprising MS-A, and IStream2 comprising MS-B. In some such embodiments, the user creates I Stream1, selects MS-A, and sets the flow rate. The user also creates I Stream 2, defines the components and makeup of MS-B (by percentage, ratio, mass fraction, mole fraction, etc., or simply selects a pre-defined custom mixed specie, as above), and sets the flow rate. The user then adds a mixer unit operation to combine the two streams, and the software applies pre-defined rules and equations to determine the resulting composition of the combined stream output by the mixer.

In preferred such embodiments, the output of the mixer is stored in the external layer (user selected/defined species and source allocation thereof), and transformation objects are stored containing data sufficient to apply pre-defined rules and equations to calculate the middle layer (expanded components list comprising all component-source combinations), and the internal layer (unique components list comprising combined unique components).

Middle Layer

The "middle layer," also referred to as the "intermediate layer" or "source-specific layer," maintains the full source-specific table of data, and explicitly allows duplicates. For every stream accessible to the user, as well for hidden streams in some embodiments, the program will maintain a mapping between the external and middle layer. The middle layer is an "expanded" or "broken-out" component list, comprising all component-source combinations.

For the purpose of illustration, consider the example where a user defines two sources in the external layer, Source A and Source B, and defines Source A as a mixed specie comprising pentane and methane, and Source B as a mixed specie comprising pentane, and octane. The middle layer would then comprise: pentane-A, methane-A, pentane-B, and octane-B.

The internal-middle transformation object comprises mapping to the internal layer for pentane-A and pentane-B, for example, such that they are combined simply as pentane in the internal layer. The external-middle transformation object comprises mapping between pentane-A and methane-A to Source A, and pentane-B and octane-B to Source B, such that they are presented combined in the external layer simply as Source A and Source B.

If an additional component was added as an individual specie, such as pentane, and not as part of a mixed specie, the middle layer would then comprise: pentane, pentane-A, methane-A, pentane-B, and octane-B.

In some embodiments unit operations not requiring total species values (i.e. not requiring to operate only on unique components and not on duplicated components) are performed on the middle layer. In some embodiments, however, at least some such calculations are still performed in the internal layer in order to increase efficiency in calculation and thereby improve the operation of the computer in simulation by reducing the number of components in the calculation.

Internal Layer

The "internal layer," also referred to as the "bottom layer," "unique components layer," "combined components layer," or "pure components layer," is a combined composition vector with no duplicates. Calculations which require total species values, in other words, calculations which are not accurate when performed on duplicated components, are performed at this layer. Such calculations include, but are not limited to, thermodynamic calculations, entropy calculations, and Gibbs free energy calculations. The internal layer contains a reduced number of components because all duplicated components are removed; therefore, calculations are both optimized for maximum speed, and are optimized for mathematical accuracy. The system must maintain a mapping, such as at least one transformation object, that converts the results of the internal layer to the middle layer and, from thence, the external layer, or directly to the external layer, or both.

The ability to preserve a single unique component in the internal layer for each unique chemical component present is of critical importance. As an example of the increased accuracy preserved, consider an embodiment taking the natural logarithm of a quantity (x) of the chemical components at a given step. If there are two components, C1 and C2, and two sources, A and B (thereby having x1A, the component attributed to source A, and x1B, the component attributed to source B, etc., where x1A+x1B=x1, or the amount from the two sources sums to the total quantity of that particular chemical component), the equation should be:

$$\Sigma xi \cdot Si - R \cdot \Sigma xi \cdot \ln(xi) \qquad \text{Equation 1:}$$

Where "$\Sigma$" represents a sum, "$S_i$" is a property related to a particular component i, "$x_i$" is the fraction of component i in a mixture, and "i" is an iterative placeholder for the component (x1, x2, etc.). In the current scenario, the second summation ($\Sigma xi \cdot \ln(xi)$) of Equation 1 becomes:

$$(x1A+x1B)\cdot\ln(x1A+x1B)+(x2A+x2B)\cdot\ln(x2A+x2B)=x1\cdot\ln(x1)+x2\cdot\ln(x2) \qquad \text{Equation 2:}$$

In other words, the natural logarithm is taken of the total quantity of a unique component, which is more accurate than, for example, if the source-allocated components were represented as different components, as in Equation 3 (representing the second summation of Equation 1 using duplicated components):

$$[x1A\cdot\ln(x1A)+x1B\cdot\ln(x1B)]+[x2A\cdot\ln(x2A)+x2B\cdot\ln(x2B)] \qquad \text{Equation 3:}$$

Clearly, Equation 3 $\neq xi\cdot\ln(xi)$. Therefore, errors are introduced using Equation 3, and potentially accumulated, amplified, or both, as the simulation progresses, because $\ln(a+b) \neq \ln(a)+\ln(b)$. In regards to natural logarithms, it is critical to calculate as shown in Equation 2 for proper accuracy. Therefore, providing at least wherein the middle layer preserves source allocation, and the inner layer preserves accurate unique components, and performing at least component-sensitive calculations from the inner layer, is critical to maintaining integrity of allocation and accuracy of calculations. Similarly, example potential inaccuracies resulting from duplicating components in selected process calculations are provided in Table 2, including example calculation types and unit operations, and example errors thereof. A few that can easily have a negative impact on safety if calculated erroneously are specifically labeled, which does not, however, indicate that other errors do not have a potential negative impact on safety.

Accordingly, rules are provided that ensure that component-sensitive calculations (calculations and methods that will return different results if duplicate components are used) are performed only on the inner layer. Such rules comprise, in various embodiments, classification of unit operations, or portions thereof, and other calculations, as component-sensitive, whether dynamically, pre-defined, or both. In various embodiments, component-sensitive calculation rules also activate transformation objects to transform the external layer to the internal layer, the middle layer to the internal layer, etc., as appropriate.

Furthermore, by providing the three different layers, the task of viewing the possible combinations of compositions is straightforward. Based on preference or permission, the user is shown the exact level of granularity of composition that is appropriate, ranging from a simplified external view of user-selected mixed and individual species, an effective internal composition of the individual unique components (individual species) of a specific stream (the internal layer), or a full source-specific dataset (such as a matrix) showing each component (individual specie) by source (the middle layer).

Stream

The chemical process models herein comprise one or more "streams." A stream carries information, entering or exiting the chemical process, or from one unit operation to the next within the chemical process. A stream represents the physical flow of one or more chemicals, or other form(s) of energy or matter (such as heat, power, etc.). Examples include a source stream, a combined stream from a mixer on the way to a heat exchanger, multiple streams leaving a separator, output streams of final products, etc.

It is important, in order to provide accurate calculations for modeling composition and allocation, that both the composition and the flow rate of each stream is known. In various embodiments and scenarios, the stream may be user-defined, pre-defined (whether visible to the user or secret), or calculated. In preferred embodiments, all input streams are user-defined or pre-defined by the user, and subsequent streams (outputs of unit operations) are calculated. In some embodiments and scenarios, enough output or intermediate streams are user-defined or pre-defined such that input streams may be calculated. Such embodiments are useful, for example, for scenario modeling, such as defining a proposed process, defining desired output streams, and calculating required input streams. In some embodiments and scenarios, at least some of: input streams, intermediate streams, output streams, or some combination thereof, are defined (composition and flow rate) by the user or pre-defined, and the missing streams are calculated based off of the selected unit operations.

Unit Operation

The chemical process models herein comprise one or more "unit operations," also referred to as "blocks." A unit operation is a single 'step' in a chemical process being modeled, typically represented by a single symbol on a process diagram. While a stream carries information, including composition information, a unit operation transforms that information via one or more calculations. Examples include, but are not limited to, input streams being combined in a mixer, a stream passing through a heat exchanger, a stream passing through a manifold, a stream passing through a separator, a stream passing through a valve, a stream passing through a compressor, and a stream passing through a vessel.

Importantly, each unit operation is performed on one or more individual species, in other words: on the molecular level. For example, while "Air" may exist for a given process in the external layer, no underlying calculations of the unit operation(s) are performed on "Air" as an entity, but on nitrogen, oxygen, etc.

It is important to note that while a unit operation is a single 'step' in a chemical process, a single unit operation will often involve multiple calculation steps. Example calculation steps and methods performed within various unit operations in various embodiments include, but are not limited to, the methods referenced in Table 3. The source of Table 3 are incorporated herein by reference for purposes relating to the calculations and methods performed in regards to chemical process composition and allocation simulation, particularly relating to calculations and methods encompassed in unit operations.

The present invention, at least in embodiments performing allocation, performs accounting around each unit operation.

Transformation Objects

Transformation objects are provided to convert between the three layers, as necessary. Transformation objects, or rules to create them dynamically, are at least partially pre-defined. The transformation objects are not necessarily simply mapping, but provide mapping between the three layers, mapping mixed species to individual species, duplicated individual species to unique individual species, etc., as appropriate to the three layers.

Each transformation object comprises the mapping rules, which are modified either internally to the transformation object, or externally when the transformation object is applied, by visibility rules. Transformation objects comprise, or are modified by, or both, in various embodiments, component-sensitive calculation rules and calculation efficiency rules, as discussed further herein.

Description of Terms Used

Following is a non-exhaustive list of specific nomenclature used in reference to the invention disclosed herein and embodiments thereof. This list is provided as an aid to understanding the invention, and should be taken in the context of the full specification. In many cases, further embodiments and specific examples disclosed elsewhere in this document will further clarify the meaning, usage, and scope of a particular term. This list of terms does not exclude descriptions of terms found elsewhere herein.

Layer

As used herein, "layer" is used, in reference to storing and manipulating chemical species, whether mixed or individual. A layer refers to a dataset, whether stored as a unique set, as part of a larger set, as a temporary set—such as is generated from one or more datasets by a query, or some combination thereof. Accordingly, "dataset" is used as an equivalent term herein, where appropriate in context. Dataset is not equivalent to database, as a dataset may comprise only a portion of a database, multiple databases, portions of multiple databases, etc.

A layer may be represented by one or more tables, but is not necessarily limited to a single table. For example, an external layer may represent all mixed species and separate individual species used in a process model. The external layer may comprise a table of all selected mixed species and may, in some embodiments, additionally comprise a table of all selected components that are publicly viewable to the user.

In some embodiments, a layer comprises multiple tables or other data storage structures. Alternatively or additionally, in some embodiments, at least some portions of multiple layers are contained in one table. For example, in some such embodiments, a single table contains all components used, with at least one column having serialized data comprising the mixed species in which each component is used, and at least one column having serialized data comprising the sources to which each component is allocated.

Allocation

As used herein, "allocation" and "source allocation" are used, in the context of process simulation, to refer to allocating a mixed specie, individual specie, etc. to one or more sources. As used herein, "source accounting," "allocation accounting," or abbreviated simply as "accounting," are equivalent terms, when used in the context of source allocation.

For example, two oil wells may both be a source of a mixed specie or a individual specie—such as pentane—with 40% of pentane from Well A, and 60% from Well B. In preferred embodiments, as the chemical process proceeds, the amount of pentane at each step is apportioned to Well A and Well B, respectively, according to the inlet proportions, and applicable calculations (e.g. thermodynamics, entropies, etc.) performed during the modeling of the process. Ultimately, the outputs of the process are allocated to Well A and Well B. In some embodiments, apportionment is performed according to various appropriate parameters.

Thus, accurate apportionment of the various output streams can be made to the various sources, and decisions made accordingly. For example, Well A may contribute more to a higher value output stream and, therefore, receive higher royalty payouts, or be more a valuable stream to purchase.

In all embodiments providing allocation, accurate allocation is maintained by performing allocation only on distinct individual species, not on duplicated components, and by performing allocation of individual species at at least one unit operation. In preferred embodiments, allocation is performed at each unit operation.

Stream properties (as opposed to stream composition) are not always necessary for accurate allocation through certain unit operations—such as mixers and splitters. In some embodiments, therefore, properties are not included in the stream for a process only requiring allocation and involving only unit operations in which allocation is not affected by the properties.

Individual Specie

As used herein, an "individual specie" is used, in the context of chemical process simulation, to refer to a "real" or "native" component, and also referred to as a "pure specie." An individual specie is also sometimes referred to as a "component," when appropriate according to context.

An individual specie is a chemical of known properties and suitable for use in process modeling, and may be an element or molecule, but is not necessarily either. An individual specie may be a compound, solution, mixture, suspension, or other suitable chemical form. Examples of individual species include, but are not limited, hydrocarbons (such as C1, C2, C3, C4, C5, C6, C7, C8, C9, C10-12, C13-14, C15-17, C18-C20, C21-23, C24-27, C28-33, C34-42, C43-80), N2, CO2, and H2O.

A "unique" or "distinct" individual specie means that the specie is not duplicated by source. For example, if Source1 comprises individual species pentane and methane, and Source2 comprises individual species pentane and methane, the duplicated individual species (by source) may be represented as source1-pentane, source1-methane, source2-pentane, and source2-methane. The unique individual species are simply pentane and methane.

Process Model

As used herein, a "process model" is a representation of a chemical process, whether visually (such as with a diagram), with computer code, or the like. In software, a process model is typically (and is so in preferred embodiments) represented by one or more object models comprising one or more objects. Such objects include, for example unit operations, or blocks, and also include streams, such as energy streams, process streams, etc.

DETAILED DESCRIPTION OF THE DRAWINGS

As with all drawings and specific embodiments presented herein, various other embodiments are disclosed directly or indirectly herein in relation to various aspects of the invention.

FIGS. 1A & 1B

Figure 1B:
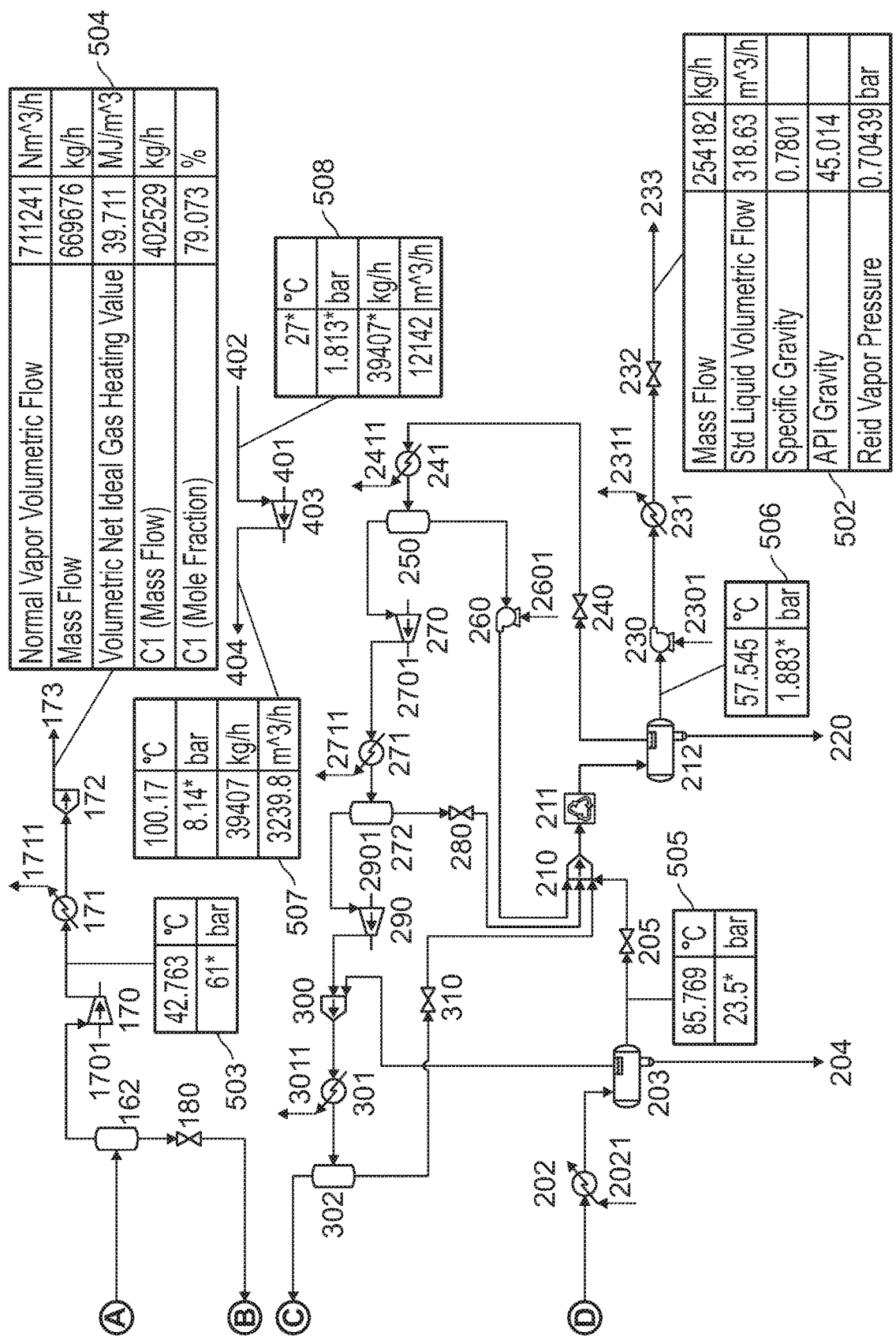
FIG. 1B is a schematic process model of a second portion of the example chemical process of FIG. 1A.

FIG. 1A and FIG. 1B, together, illustrate an example process modeled for simulation in software, in which there are four sources: Field 1 (F1), Field 2 (F2), Field 3 (F3), and Field 4 (F4). Each source is represented by a mixer (110, 120, 130, and 140) combining that field's primary stream (111, 121, 131, and 141), and produced water stream (112, 122, 132, and 142). The field output arrives in the process at a heat exchanger for each field: exchanger 113, 123, 133, and 143, with heat output streams 1131, 1231, 1331, and 1431, respectively. The F1 field stream enters Inlet A Manifold 114. The F2 and F3 field streams both enter Inlet B Manifold 124. The F4 field stream enters Inlet C Manifold 144.

The outputs from each manifold enter individual separators: Inlet Separator A 115, Inlet Separator B 125, and Inlet Separator C 145. The water output stream from the three separators go through individual valves (116, 126, and 146), and are combined in mixer 190, and exit the process as combined water stream 191. The gas output stream from the three separators (115, 125, and 145) are combined in mixer 150, the output of which goes through valve 151, and into HP Manifold 160.

The output stream from HP Manifold 160 passes through heat exchanger 161, having heat output stream 1611, then (the stream being connected between FIG. 1A and FIG. 1B by the notation "A") into vessel 162. From vessel 162, two streams exit: one into compressor 170, having energy stream 1701, and then through heat exchanger 171, having heat output stream 1711, through splitter 172, and from thence out as exiting Gas Export stream 173. The other stream exiting from vessel 162 passes through valve 180, and (the stream being connected between FIG. 1B and FIG. 1A by the notation "B") into mixer 200.

The liquid hydrocarbon output stream from the three separators pass through individual valves (117, 127, and 147), and are combined in mixer 200. The output of mixer 200 passes through recycler 201 (the stream being connected between FIG. 1A and FIG. 1B by the notation "D"), then heat exchanger 202, having heat output stream 2021, and enter Stage 2 Separator 203.

Stage 2 Separator 203 outputs a water stream 204, a condensate stream into valve 205, and a gas stream into mixer 300. Mixer 210 combines other inputs (discussed elsewhere herein) and passes the output into recycler 211 and then into Stage 3 Separator 212. Separator 212 outputs water stream 220. Separator 212 also outputs a condensate stream into pump 230, having energy input stream 2301, then into heat exchanger 231, having heat output stream 2311, then through valve 232, exiting as final Condensate Export stream 233. Separator 212 also outputs a gas stream through valve 240, then heat exchanger 241, having heat output stream 2411, and into vessel 250. From vessel 250, the stream splits: one stream passes through pump 260, having energy input stream 2601, and into mixer 210, the other stream passes through compressor 270, having energy stream 2701, then heat exchanger 271, having heat output stream 2711, and into vessel 272.

From vessel 272, two streams exit: one through valve 280 and into mixer 210, and the other through compressor 290, having energy stream 2901, and into mixer 300. From mixer 300, the stream from compressor 290 and the gas stream from Stage 2 Separator 203 are combined and pass through heat exchanger 301, having heat output stream 3011, and then into vessel 302. From vessel 302, two streams exit: one goes through valve 310 and then into mixer 210, and the other (the stream being connected between FIG. 1B and FIG. 1A by the notation "C") passes through compressor 320, having energy stream 3201, and then enters HP Manifold 160. Additionally, the process has a compressor 403, having energy stream 401, the compressor receiving input 402, and outputting compressor test stream 404.

In preferred embodiments, modeling software provides visible output of calculations to the user at various points. Visualization 501 shows calculated mass flow of the exiting water stream 191. Visualization 502 shows calculated properties of exiting Condensate Export 233, properties including Mass Flow, Standard Liquid Volumetric Flow, Specific Gravity, API Gravity, and Reid Vapor Pressure. Visualization 503 shows pressure and temperature of the output of compressor 170 before entering exchanger 171. Visualization 504 shows calculated properties of exiting Gas Export stream 173, properties including Normal Vapor Volumetric Flow, Mass Flow, Volumetric Net Ideal Gas Heating Value, C1 (Mass Flow), and C2 (Mole Fraction). Visualization 505 shows pressure and temperature of the condensate stream exiting Stage 2 Separator 203 before entering valve 205.

Visualization 506 shows pressure and temperature of the condensate stream exiting Stage 3 Separator 212 before entering pump 230. Visualization 507 shows properties of compressor test stream 404 exiting compressor 403, properties including temperature, pressure, mass flow rate, and volumetric flow rate. Visualization 508 shows properties of input stream 402 before entering compressor 403, properties including temperature, pressure, mass flow rate, and volumetric flow rate.

FIG. 2

Figure 2:
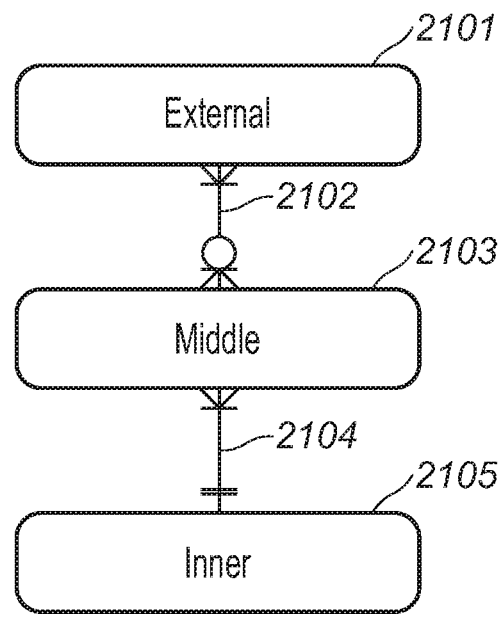
FIG. 2 is an example entity-relationship diagram of the relation of the three-layer structures in various embodiments.

FIG. 2 illustrates, via an entity-relationship diagram, an exemplary layer configuration used in preferred embodiments. External layer 2101 has a one-or-many to zero-or-many mapping 2102 to middle layer 2103. Middle layer 2103 has a one-or-many to one-and-only-one mapping 2104 to inner layer 2105. The external layer comprises composition names and is visible to the user.

FIG. 3

Figure 3:
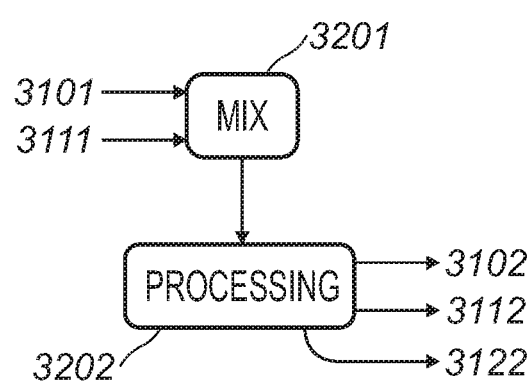
FIG. 3 is a simplified general process model diagram.

FIG. 3 illustrates a simplified process diagram. Input streams 3101 and 3111, are mixed together in mixer 3201. The resulting stream is then processed through one or more processing steps 3202, and at least two output streams are output: output stream 3102, output stream 3112, and optional output stream 3122.

In some embodiments, input streams 3101 and 3111 represent two different sources, Source A, and Source B, respectively. In some such embodiments, output stream 3122 is further processed. Output stream 3102 is valued at $X/Standard Cubic Foot (SCF). Source allocation accounting allows the value contributed by each source to be determined: $X•A3102 and $X•B3102, where the subscript "3102" indicates the proportion of output stream 3102 allocated to Source A. Similarly, output stream 3112 is valued at $Y/SCF, and the value contributed by each source is calculated as $Y•A3112 and $Y•B3112. In various embodiments, this calculation is presented on a component, source, or composition level, or some combination thereof.

Accordingly, the value to the process of each source may be determined. For example, if output streams 3102 and 3112 are the only two output streams contributing to the value of the process, Source A is valued at $X•A3102+$Y•A3112, and similarly for Source B.

FIG. 4

Figure 4:
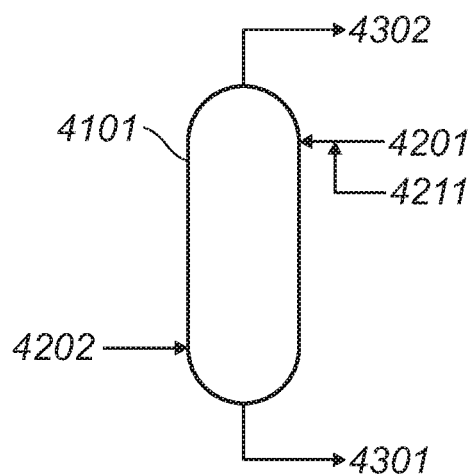
FIG. 4 is a simplified amine sweetening operation.

FIG. 4 illustrates a simplified process diagram representing a unit operation for acid gas removal, simulated in some embodiments. Gas treatment tank 4101 receives gas input stream 4202, and solvent input stream 4201. It further receives, in some embodiments, secondary solvent input stream 4211, although in some embodiments, secondary solvent input stream 4211 is not included. The treated gas exits as treated gas output stream 4302, and the remainder exits as output stream 4301.

In some embodiments herein, the solvent input stream 4201 comprises a proprietary amine mixture, referred to here as "Solvent A." Solvent A is included in the external layer, and the components of Solvent A are pre-defined in the simulation software, either before the user receives the software or afterwards (such as via a proprietary composition file defining the components in a way indecipherable by the user). The components are included in the middle and internal layers, but the components attributable to Solvent A are prevented from being reported to the user: the user cannot see a component breakdown that includes components attributed to Solvent A.

Output stream 4301 comprises parts of the solvent stream (including Solvent A), as well as other components, such as H2S and CO2. Any display accessible by the user only shows the known components (such as of the gas stream) and the composition Solvent A by name, but does not show the components attributable to Solvent A, whether viewing inputs or outputs of process unit operations.

In many embodiments comprising secondary solvent input stream 4211, there are overlapping unique components in both input streams 4211 and 4201. In embodiments where at least one comprises a proprietary mixture, the components attributable to the proprietary mixture are hidden from the user, and only the mixture name and appropriate attributes (quantity, etc.) are reported. However, the portion of components not attributable to the proprietary mixture—even for components shared with the proprietary mixture—are visible by the user. For example, if Solvent A in input stream 4201 comprises diethanolamine (DEA), and input stream 4202 is not proprietary and comprises DEA, the portion of DEA allocated to input stream 4202 is visible to the user, but the portion of DEA allocated to Solvent A is concealed from the user, and only Solvent A as a composition is visible.

Similarly, in embodiments where input stream 4211 comprises a proprietary composition different than that of input stream 4201, the components attributable to proprietary mixed species are preserved secret from the user, using the middle layer for allocation accounting, the internal layer for calculations using unique components only, and the external layer for user-selected mixed species and individual species. The names of the components of the proprietary composition(s) are not visible to, nor accessible by, the user unless the components are also used in non-proprietary mixed species or individually added as non-proprietary individual species. The amount of the individual components of the proprietary composition(s) allocated thereto are not visible to, nor accessibly by, the user, regardless of whether the names of the components are visible because added as part of a non-proprietary composition or as non-proprietary components.

For all such embodiments, the allocation of each component to the appropriate proprietary mixture is maintained in the middle layer, while component-sensitive (such as relevant entropy, Gibbs free energy, etc. equations) calculations are performed using the inner layer containing the combined unique components. User reporting for the proprietary mixture is provided at least partially via the external layer.

FIG. 5

Figure 5:
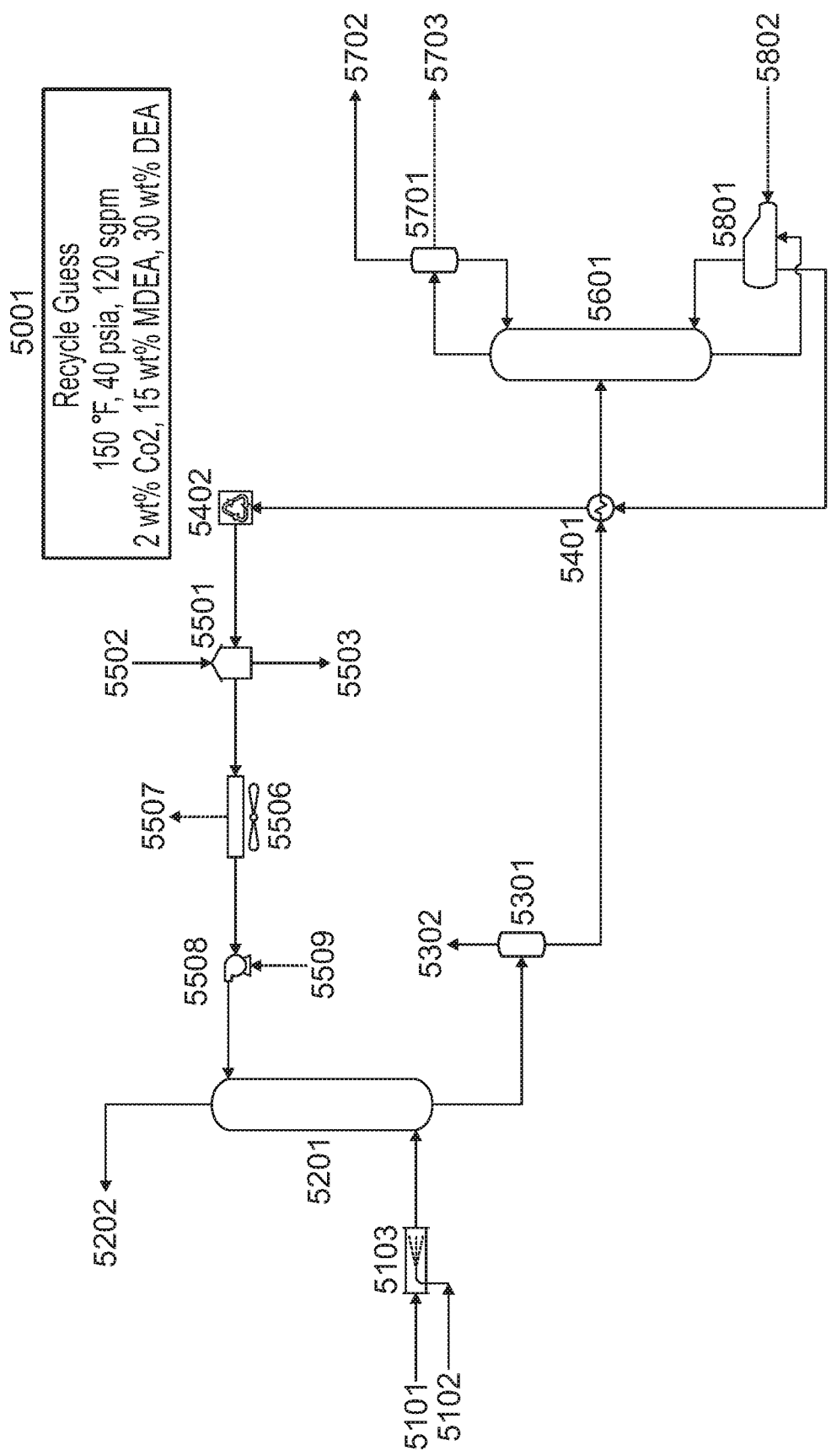
FIG. 5 is a schematic process model of an example amine sweetening process.

FIG. 5 illustrates a simplified amine-sweetening process with mixed amine, simulated in some embodiments. Dry Basis Sour Gas input stream 5101 and Saturant (Water) input stream 5102 both enter Saturator 5103. The Sour Feed output stream from the Saturator enters Absorber 5201. Sweet Gas output stream 5202 exits the Absorber 5201, as does the Rich Amine output stream, entering Rich Flash tank 5301. Flash Gas output stream 5302 exits the tank, as does an output stream entering the Lean/Rich Exchanger 5401.

One output stream from Lean/Rich Exchanger 5401 enters Stripper tank 5601, from which exits an output stream into Condenser tank 5701, and a stream returns from the Condenser 5701 into the Stripper tank 5601. Additionally, Acid Gas output stream 5702 exits the Condenser 5701, as does a Q Condenser (energy) output stream 5703. Another output stream exits Stripper tank 5601 and inters Reboiler 5801. Reboiler 5801 also receives Q Reboiler (energy) input stream 5802, and has two output streams: a stream into Stripper tank 5601, and a Lean Amine stream into Lean/Rich Exchanger 5401.

A second output stream from Lean/Rich Exchanger 5401 enters Recycle 5402. Recycle Guess output stream from Recycle 5402 enters Amine Makeup 5501. Amine Makeup 5501 also receives Makeup stream 5502, and has two output streams: Blow-down output stream 5503 and an output stream into Trim Cooler 5506. Trim Cooler 5506 has two output streams: Q-1 (energy) output stream 5507, and an output stream into Circulation Pump 5508. Circulation Pump 5508 also receives P-1 (energy) input stream 5509, and has a single output stream into Absorber 5201.

Display 5001 shows properties of the Recycle Guess stream exiting Recycle 5402 and entering Amine Makeup 5501.

In an exemplary method, the user inputs the process diagram, such as by drag and drop of unit operation schematic symbols (Exchanger, Stripper tank, Reboiler, etc.), and defines the input and output stream(s) compositions for each unit operation in the external layer. The user also defines a sufficient number of stream compositions to complete the simulation—in most scenarios, the user defines the original input streams (e.g. 5101 and 5102, and in some embodiments one or more of 5509, 5802, and 5502, although in some embodiments one or more of 5509, 5802, and 5502 are pre-defined).

The software transforms to the middle layer, the internal layer, or both, as required in various embodiments, to transform each stream according to the pre-defined rules and calculations associated with each unit operation. The rules and calculations for each unit operation are typically pre-defined in the software, whether originally packaged with the software, or added by additionally installed or dynamically loaded modules. In some embodiments, the user is able to pre-define custom unit operations, with associated stream transformation rules and calculations.

FIG. 6A

Figure 6A:
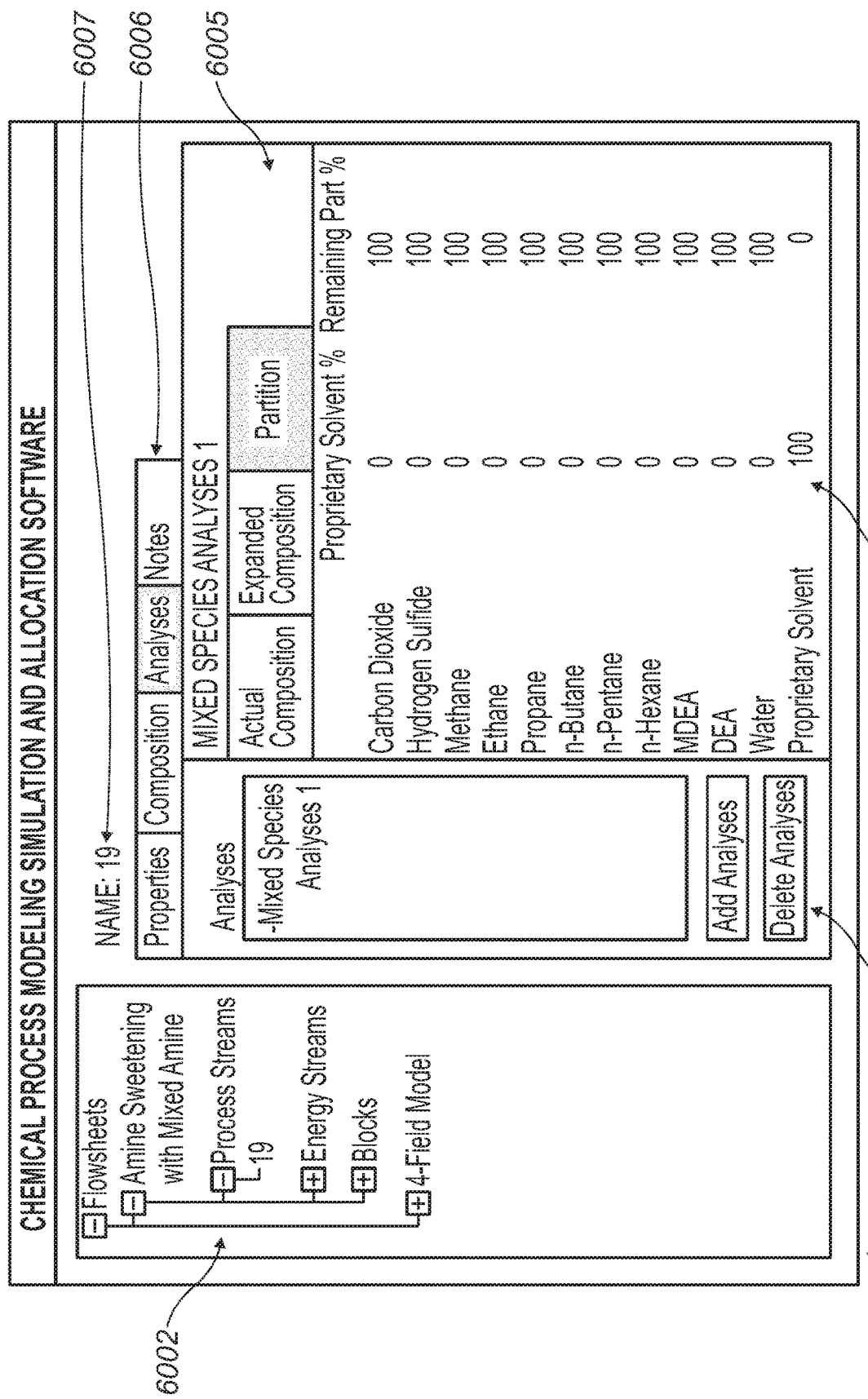
FIG. 6A is a simplified drawing of an example graphical user interface (GUI).

FIG. 6A is a simplified illustration of a software GUI used in various embodiments.

Display window 6001 contains a navigation panel 6002. The navigation panel 6002 comprises a listing of available flowsheets (a flowsheet being a schematic diagram representing a process being modeled) as a hierarchical list (also referred to as a "tree list"). The currently active flowsheet, referred to in the list as "Amine Sweetening with Mixed Amine," corresponding to the process model in FIG. 5, is expanded out to show the sub-items "Process Streams," "Energy Streams," and "Blocks," each of which are collapsed, but may be expanded to display the streams and blocks (unit operations) in the active flowsheet. Likewise, the "4-Field Model" flowsheet, corresponding to the process model in FIGS. 1A and 1B, is not active, but may be activated and expanded by the user to show the streams and blocks headings, etc.

The area to the right of navigation panel 6002 may show the process schematic diagram, such as are shown in FIGS. 1A, 1B, and 5. In the present figure, it shows a details display and a stream identifier 6007. Stream identifier 6007 shows that stream 19 (which is the actively selected stream, and is also shown in the hierarchical list in navigation panel 6002) is currently selected and is the subject of the detail display. The stream identifier is, in some views a process stream identifier, energy stream identifier, block identifier, etc., as appropriate. In some views, the stream identifier is not present.

The detail display in the figure comprises upper-tabs 6006 presenting the user the option of choosing between viewing properties, composition, analyses, or notes. Analyses are currently selected. Selection panel 6003 shows the currently available analyses, as well as the option to delete an analysis, or add an analysis (including, but not limited to: amine analysis; choke analysis; combustion analysis; composition subset; control valve; differential pressure flow meter; distillation curves; freeze out, hydrate, $H_2O$ dew point; fuel properties gas well IPR analysis; ionic info analysis; line sizing; mixed species analysis; oil well IPR analysis; phase envelope; pipe leak analysis; relief valve sizing; salt deposition analysis; shortcut distillation; and vapor pressure, dew, bubble point).

"Mixed Species Analysis 1" (of stream 19, as shown in stream identifier 6007) is the only analysis currently available, and is selected. The name "MIXED SPECIES ANALYSIS 1" is displayed above inner-tabs 6005. Inner-tabs 6005 allow the user to select from several displays of the analysis: the actual composition, the expanded composition, or a partition view. The Partition view is currently selected, and shows a table, in analysis display 6004, comparing the various species to one or more selected mixed species by percentage. Proprietary Solvent is a proprietary mixed species, so the software visibility rules prevent individual components of Proprietary Solvent being shown. Instead, Proprietary Solvent is shown always and only as a single entry, without revealing its constituent individual species.

The composition tab in upper-tabs 6006 allows the user to view stream composition. Selection panel 6003 shows "GROUPING" choices, such as to view the composition by "Basis" or "Phase," as well as options to "Specify" grouping and to group by "Ionic Info." Further tab options allow the user to view composition by mole fraction, molar flow, mass fraction, or mass flow. Flow rates (e.g. molar flow, mass flow, standard vapor volumetric flow, normal vapor volumetric flow, and standard liquid volumetric flow) are shown in an additional panel, when applicable. Composition is shown, for example, when "Basis" grouping and "Mass Fraction" is selected, with columns comprising total (%), vapor, light liquid, heavy liquid, and mixed liquid.

The properties tab in upper-tabs 6006 allows the user to view stream properties. Selection panel 6003 disappears, and various stream properties are presented, such as, but not limited to: temperature, pressure, mole fraction vapor, mole fraction light liquid, mole fraction heavy liquid, molecular weight, mass density, molar flow, mass flow, vapor volumetric flow, liquid volumetric flow, standard vapor volumetric flow, standard liquid volumetric flow, compressibility, specific gravity, API gravity, enthalpy, mass enthalpy, mass Cp, ideal gas Cp/Cv ratio, dynamic viscosity, kinematic viscosity, thermal conductivity, surface tension, net ideal gas heating value, net liquid heating value, gross ideal gas heating value, and gross liquid heating value. Properties are shown, for example, with columns comprising total, vapor, light liquid, heavy liquid, and mixed liquid.

FIG. 6B

FIG. 6B is an illustration of a portion of a GUI, such as is in FIG. 6A. The analysis display 6101 is the display replaces that of analysis display 6004 in FIG. 6B when the "Actual Composition" tab of inner-tabs 6005 is selected in FIG. 6A. The actual composition typically shows the external layer. The expanded composition (not illustrated) would show the middle layer, except when proprietary mixed species are used, when visibility rules prevent the middle layer composition of the proprietary mixed species from being viewed by the user.

EXAMPLE EMBODIMENTS

Example Process Modeling Method

In various embodiments of allocation, a personal computer is provided with chemical process simulation software (CPSS). The CPSS is provided with at least one dataset viewable in at least three layers: an external 'user-interaction' layer, a middle 'source-specific' layer, and an internal 'unique-components' layer. In various such embodiments, the layers are all in a single database structure, are in a single table, are in separate tables, are in separate databases, are in a text file, an encrypted file, a non-structured database, or other suitable data structure.

The external layer contains one or more species, each specie representing one or more individual chemical components. The middle layer comprises each individual specie in the external layer, whether added to the external layer as an individual specie or as part of a mixed specie, identified by the original source of the component (e.g. Field 1, Well A, etc.). The internal layer comprises every unique individual specie in the middle layer, not differentiated by source. Put another way, the external layer comprises stream composition information, where the composition information is represented as mixed species and individual species, correlating to the way the user defines the input stream composition information in the external layer to begin with. The middle layer comprises an expanded list of every combination of stream sources and components (individual species). The internal layer comprises a combined list having the total of every unique component (total individual specie) in the stream(s).

The user sets up a chemical process to model, such as is discussed above, using known methods. In some embodiments, the user creates a process using Microsoft® Visio®. In such embodiments, the CPSS integrates with Microsoft Visio and is provided additional information on the process by the user through an extended Visio interface.

The user identifies, as necessary, sources, compositions of source streams, process unit operations (such as compressors, pumps, valves, separators, etc.), etc. The user identifies desired model outputs, such as process component properties (e.g. temperature, pressure, mass, flow, etc.) In preferred embodiments, once complete, the user triggers the CPSS to calculate the outputs from the inputs provided, including the process.

In various such embodiments, presuming the inputs provided are sufficient, the CPSS progressively applies each unit operation (or multiple unit operations) to transform one or more input streams in the process to output streams using at least a three-step iterative method, beginning with source streams. For example, in FIG. 1A and FIG. 1B, the properties of F1 input stream 111 (e.g. a hydrocarbon stream with nitrogen), F1 Produced Water stream 112, F2 input stream 121 (e.g. a different hydrocarbon stream with nitrogen), F2 Produced Water stream 122, and so on for F3 and F4, are provided by the user. The user inputs the composition information for each of the source streams into the external layer. In preferred embodiments, each input stream composition, representing a source intended to be tracked, is input as a mixed specie. In some such embodiments, the stream composition mixed specie itself comprises mixed species.

It should be noted that, in some embodiments, all source streams are tracked. However, in some embodiments, not all source streams are tracked. For example, if two different source streams provide nitrogen, but it is not useful to the user to track the allocation of nitrogen, the user does not mark the relevant streams for allocation tracking (or, alternatively, marks the relevant streams as not being tracked). Such embodiments allow improvement of efficiency by allowing some sources to not be tracked, thereby preventing the necessity of keeping those as duplicated individual species in the middle layer. In some embodiments, any species added to an input stream, but not defined as a mixed specie (even if the 'mixed specie' only contains a single individual specie), will not be tracked for allocation purposes.

One or more transformation objects are created by the CPSS to generate the middle layer, such that the middle layer comprises accurate information on each individual specie, and the source thereof. Similarly, at least one transformation object is created, as necessary to generate the internal layer, such that the internal layer comprises accurate information on each distinct individual specie comprising the present stream. In preferred embodiments, the information comprises not only composition data but further comprises properties of at least some of the species.

The unit operation comprises transformations to the stream compositions, such as thermodynamic calculations and, in preferred embodiments, is performed on either the middle layer or internal layer. Performing unit operations adversely affected by duplicated components on the internal layer is important to preserve accuracy by having each chemically distinct component represented only as a single individual specie, and represented according to original source (or other appropriate allocation scheme), and to optimize speed and efficiency of the computer by reducing exponentially increased operations required by duplicated components.

Once the base calculations are performed (compressor power, pump loss, etc.), the middle layer is updated, if required, by one or more transformation objects. The transformation object applies pre-defined rules to allocate the unique components to the various appropriate sources for each component, commensurate with the proportion of the source. Thereby, an accurate middle layer is maintained, proportioning each component according to its original source.

The external layer is similarly updated, either by a transformation object(s) from the middle layer, or by a transformation object(s) from the internal layer, at least by updating the quantities of each specie at the given step. In preferred embodiments, the stream compositions are maintained at least at the external layer, with transformation objects being maintained for the middle and internal layers. In some such embodiments, the stream composition is maintained at the inner layer level, middle layer level, or both. However, in some embodiments, the stream compositions are maintained at least at the middle layer, and transformations are maintained to update the internal layer and external layer dynamically as required. Similarly, in some embodiments, the stream compositions are maintained at the inner layer level, and transformation objects are maintained for each stream to update the external layer and middle layer, as required.

Thus, the user provides input to the external layer, and the CPSS transforms it to the middle layer and inner layer. The properties of the various streams (111, 112, 121, 122, 131, 132, 141, 142), after passing through mixer 110, 120, 130, and 140, are calculated as individual species according to the relevant thermodynamic, entropic, etc. calculations, and are calculated at either the internal or middle layer. In preferred embodiments, mixer unit operations are calculated at the middle level. The necessary transformation objects are created, updated, or both. The compositions of the output streams from the unit operation are generated, updated, or both, at least at the external layer, and the CPSS moves to the next unit operation, e.g. the exchangers (113, 123, 133,143).

The three-layer abstraction (internal, middle, and external layers) allows the CPSS to progressively calculate each step, as it evaluates the process model, with maximum accuracy and speed, and at the same time allows the user at least to view allocations of each individual specie by source (via the middle layer) and of each mixed specie, by source, if desired (at least from the external layer), and to view the total of each individual specie (at least from the internal layer), and to view the total of each mixed specie (at least from the external layer).

User Viewing Permissions

In preferred embodiments, such as in the method discussed immediately above, specific visibility rules are implemented in the software determining what the user may view. For example, in the preceding example method, the user may view: (1) the mixed species the user added to the external layer, as mixed species and not as individual species making up the mixed species, and (2) the individual species the user listed in the external layer individually and not as part of a mixed specie.

Furthermore, the user may view any non-proprietary species making up the composition of the stream as a result of a unit operation. For example, in an example amine-sweetening process, two input streams enter an absorber tank: a mixed specie of "Sour Gas" and a mixed specie of "Proprietary Amine Solvent." Two output streams exit the absorber tank: a non-proprietary mixed specie of "Sweet Gas" and a recapture stream comprising: "Proprietary Amine Solvent," H2S, and CO2. The user may view the composition of the recapture stream, and see the H2S and the CO2, resulting from the transformation to the input streams by the absorber tank unit operation. However, the user may not view the composition of the "Proprietary Amine Solvent" mixed specie.

Additionally, the user may view the chemical components (individual species) of non-proprietary or publicly-known mixed species (such as air) in the middle layer. The user may not view the chemical components (individual species) of proprietary mixed species whose chemical composition is not publicly known, but whose chemical composition has been entrusted to authorized personnel for inclusion as pre-defined mixed species. Specifically, the user cannot view the makeup of the proprietary mixed specie in the middle layer or the internal layer. While the transformation objects between the layers can work directly with the individual species, as appropriate, rules and instructions are provided that recombine the individual species of mixed species when the user views the layers, even in the middle or internal layers.

Furthermore, the user may add additional mixed species in the external layer, so long as the chemical composition thereof is known to the user. In some embodiments, the user may add proprietary mixed species by means of providing one or more files—such as a file(s) provided by a software vendor; by a third-party vendor; by the vendor, manufacturer, or distributor of the proprietary mixed species; etc.— in a format(s) known to the CPSS which provides the CPSS with the chemical components and proportions necessary for accurate calculations, while preserving the secrecy of the components from users. In some embodiments, users may also add non-proprietary mixed species using one or more files in a format(s) known to the CPSS, for convenience and ease of use, and to facilitate interchange of mixed species composition information. In some such embodiments, the file format(s) is an industry-standard format. In various embodiments, alternatively or additionally, the user can add one or more mixed species in at least one user interface of the CPSS.

Example Stream Composition Representation and Storage

In some preferred embodiments, the stream compositions are maintained in a given layer as tables corresponding to each stream, the relevant tables being updated upon completion of a unit operation. In some embodiments, unique composition tables are maintained in the external layer, and the quantities and other characteristics are updated in those tables in the external layer after each unit operation is completed. Transformation objects create the middle layer and internal layer as required.

In some embodiments, the streams and, in some such embodiments the species, are treated as objects (in reference to object-oriented programming). In such embodiments, the stream would have certain characteristics and various applicable methods. The unit operations would comprise methods. In various embodiments in which species are objects, characteristics would include streams of which the specie was a member, and related quantity, temperature, pressure, etc. Some such embodiments would also include the parent mixed specie(s) (if any) among the characteristics. [0126]

In some embodiments, each source-referenced individual specie is a separate object (e.g. Nitrogen-Air, Nitrogen-Gas1, Oxygen-Air, Methane-Gas1, etc.), with characteristics including the unique individual specie of that object (e.g. Nitrogen, Oxygen, Methane, etc.). Various other embodiments additionally or alternatively utilizing known programming techniques are further contemplated herein in regards to stream composition using a system with at least three layers, and related methods.

Illustrative Computer Efficiency Improvements

In preferred embodiments, rules are provided using the three layers (external, middle, internal) to increase the speed with which the computer completes a chemical process model simulation. In some such embodiments, the unit operations are performed primarily and, in some embodiments, are performed exclusively, on the middle and internal layers.

Specifically, rules are provided for performing unit operation calculations (such as compressor power, separation, mixing, etc.) on the middle layer when the number of components do not have a significant correlation with calculation time, and on the internal layer when the number of components have a significant correlation with calculation time. The threshold to reach 'significant' correlation to calculation time depends, at least in part, on the processing cost of the relevant transformation object(s).

For example, the speed of many calculations is inversely proportional to the square of the number of components included in the calculation. Calculations involving nested loops are an example. In cases where the transformation object from external to internal involves breaking apart each listed specie into its constituent individual species, and combining any duplicate individual species into a single entry, the cost of calculation is fairly straightforward—often a linear relationship to the number of constituent species by listed species (e.g. an external layer of Mixed Species A having pentane and methane, Mixed Species B having pentane and methane, and individually listed methane, would have 2+2+1=5 constituent species, and only 2 unique individual species). The cost of calculation for transforming to the middle layer would also be fairly straightforward, often a linear relationship depending on the number of constituent species, but not requiring the combination of duplicate individual species, or at least not the same amount of combination.

If a unit operation involves, for example, a two-layer nested loop over all the components in a layer ("N" components), the cost of calculation is related by $N^2$. Thus, in preferred embodiments, if the transformation cost is linearly related to N, and the unit operation cost is related to an exponent of N, the stream composition is transformed to the internal layer, and the unit operation is performed thereon. Accordingly, the functioning of the computer is improved by exponentially improving the speed of that unit operation in the simulation. Most chemical process simulations involve multiple unit operations. The more unit operations (or parts thereof) that can similarly utilize the internal layer, the more time savings are realized, and the results combine to greatly increase the speed of the overall simulation. Persons of ordinary skill in the art will easily appreciate the improvement, especially when it is considered that typical pipeline gathering processes involve between 4 and 500 unit operations, and each unit operation often involves multiple calculation steps.

Therefore, in preferred embodiments, the program is provided with calculation efficiency rules—in various embodiments pre-defined, dynamic, adaptive, or some combination thereof—that implement a known algorithm performance or complexity analysis or classification (a particular example of which is order of the function classification, often referred to as "Big-O" analysis or classification). The rules evaluate or classify the efficiency of the transformation object(s), and of the unit operation (in various embodiments: as a whole, as specific portions of the unit operation, and combinations thereof). Based on the result, the unit operation is accordingly performed on the middle layer or on the internal layer.

Notwithstanding, in general, component-sensitive calculation rules have priority over calculation efficiency rules, in order to preserve simulation accuracy. Some embodiments, however, are provided with at least one mode allowing the user to prioritize speed over accuracy, and alerts users that the calculation accuracy may be negatively affected in that mode. In such a speed-priority mode, the rules of calculation efficiency take priority, and unit operations are performed on the middle layer or internal layer based primarily on the calculation speed. In some such embodiments, one or more error-tolerance parameters may be set, either pre-defined, user set, or both, to allow calculation efficiency rules to prioritize only when the expected impact on error is below a certain threshold. Such a threshold, in some embodiments, operates on dynamic classification of unit operations or portions thereof according to one or more error estimation algorithms. In some embodiments, such a threshold operates on pre-defined classification of unit operations or portions thereof. In some embodiments, both pre-defined and dynamic classification issued.

In general use, real-world composition and allocation process simulation, such as hydrocarbon refinement processes from multiple wells, is performed in times on the order of minutes. In contrast, the same simulations, using only the equivalent of the middle layer (duplicated individual species by source) instead require significantly longer times, with the time requirement roughly proportional to the number of components.

In some embodiments, composition (and properties, as necessary, such as thermodynamics, flow rate, etc.) are defined at one stream, whether defined by the user or calculated by the software, and the software directly translates the composition, properties, or both along the stream, and through unit operations that do not change the composition, properties, or both. This improves efficiency of the computer by avoiding unnecessary calculations and transformations. In preferred such embodiments, if the user has not requested a view in another layer at a particular stream or unit operation, and no calculation is necessary, no transformation between layers is performed at that unit operation(s).

In various such embodiments, unit operations comprise data on calculations required. Rules are defined, such as embedded in the software, pre-defined in the software, added by the user, etc. that allow compositions and properties to pass unchanged through unit operations. For example, the composition of a stream going through a valve would be unchanged. A pre-defined rule is provided that a single stream passing through a valve does not include any transformation to the stream composition. In some embodiments, the transformation simply does not contain any instructions for transforming the composition data of the stream, and the stream composition data passes through unchanged.

Example Use Cases

Three sets of embodiments addressing three example key use cases are provided here below. These embodiments and use cases are taught individually for clarity and simplicity in explanation.

However, in various embodiments, various combinations and variations thereof are contemplated. For example, in some embodiments, proprietary mixed species are used and allocated to sources. Some such embodiments use known mixed species. Some embodiments use known mixed species (such as air), attributed to sources, and some such embodiments use proprietary mixed species, such as for treatment unit operations in the chemical process.

Known Composition

In various embodiments, means, methods, or both, are provided for modeling a chemical process using a material where the underlying composition is generally known and relatively complex. An example of this would be air. It is simpler for the user to add the mixed specie 'air' to a list of chemicals than include all the components associated with air, and then fill out their respective amounts. Therefore, in some embodiments, for example, the mixed specie 'air' is pre-defined, and the user simply adds the specie to a list, such as of available chemicals for the model, or such as a list associated with a particular source or unit operation, and begins using it. The constituent individual species (components) are automatically included in the middle layer and internal layer, as applicable, by the software, via transformation objects.

Source Composition

In various embodiments, means, methods, or both, are provided for representing origin of a material, such as a natural gas or crude oil source. In various chemical processes modeled in such embodiments, the oil or gas is made of a great number of constituent compounds that also make up other oils and gases in the chemical process to be modeled. Thus, the user and software is able to maintain the pedigree, or source, of such 'redundant' compounds, while maintaining calculation accuracy, as discussed elsewhere herein, by maintaining the three-layer system of display species (external layer), source-specific individual species (middle layer), and unique individual species (inner layer).

Proprietary Mixed Species

In various embodiments, means, methods, or both, are provided such that a user may use a proprietary mixture for accurate, component-level calculations, without the user actually knowing the components thereof. In such embodiments, a vendor of a proprietary mixture makes that mixture available to simulation users while not revealing the underlying proprietary composition. When the user desires to simulate the proprietary mixture, the user adds the name of the proprietary mixture to the component list, thereby including it in the external layer, and the user sees it as a single material. However, while displaying a single composition name, a mixed specie, to the user, the software maintains the underlying composition of that mixture as it is used throughout the simulation, even as the quantity of mixture, the mixture proportions, other properties, or some combination thereof, are changing due to separations or reactions.

Allocation Accounting

In preferred embodiments, allocation accounting is performed on calculations of intermediate steps, and not solely on a final step. In particularly preferred embodiments, accounting is performed on each and every intermediate calculation, and not only on selected steps. In such particularly preferred embodiments, the entropy calculation, compressor calculation, etc. is performed using the inner layer (unique components), and then accounting is performed to update the allocation at that step of relevant components to each source in the middle layer.

In some embodiments, accounting is performed at each step, as a process model is evaluated, but a record is not maintained of the allocation of components to each source at that step. Instead, certain steps are designated—automatically according to pre-defined rules, by the user, or some combination thereof—to store the allocation, such as at output steps, particular steps of interest, etc. The allocation of the components at that step are maintained in the middle layer, or at least in a dataset linked to the middle layer.

It is significant that accounting is performed in the process simulation, not after the simulation is completed. In other words, for each step, the calculation is performed, and accounting is performed, before moving to the next step (such as a unit operation) of the process model. Thus, it is critical to the proper functioning of the simulation, particularly to maintain accuracy, that accounting and simulation are performed together: in other words, that source allocation accounting is integral to the simulation process.

Allocation accounting itself is important because allocation is not a simple source proportion. In other words, if Source A contributes 40% of a given component, and Source B contributes 60% of that same component, that does not mean that the proportion of that component in the final output stream is necessarily 60% attributable to Source B and 40% attributable to Source A.

Depending on the amount of each component in a given physical state from each source, on the results of processing steps to each source, etc. an output stream M may be 80% attributable to Source A, and 20% attributable to source B, and an output stream N may by 25% attributable to Source A, and 75% attributable to Source B. If output stream M is a higher value output than output stream N, then the 40% contribution from Source A is potentially actually a higher value input than the 60% of Source B, because Source A contributes more to the higher value output stream. Accordingly, Source A may be preferentially purchased, or may be purchased at a higher price per unit than Source B. Thus, it is important both to the source owner(s), and to the process operator(s), in order to maximize efficiency and profit, that the source allocation accounting be as accurate as possible.

Secret Streams

In some embodiments, the modeling software is provided with the ability to keep one or more streams secret. Such secret streams are used, for example, to preserve the confidentiality of proprietary mixed species. For example, if a unit operation involving a proprietary mixed specie is a reaction, and the mixed specie gets split during the reaction, in some embodiments a secret stream is created that contains one or more of the split components from the propriety mixed specie. Thereby, the secret stream prevents components from being exposed.

Furthermore, in some embodiments, secret streams and secret unit operations are created automatically according to dynamically applied pre-defined rules and rule sets to accurately calculate a visible unit operation involving one or more proprietary mixed species. The secret stream(s) and secret unit operation(s) are calculated, but no part of the layers—external, middle, or internal—are visible to the user.

Multiple Mixed Species

All embodiments herein provide for the use of multiple mixed species. The mixed species are entered in the external layer (the user interaction layer) by the user, and the individual species thereof, by the source mixed specie, are provided in the middle layer by a transformation object(s). The vector of unique individual species is provided in the internal layer by a transformation object(s).

The ability to have multiple mixed species but calculate by individual unique species, as necessary, provides the solution to various problems, discussed elsewhere herein, including facilitating source composition entry, and source allocation, while maintaining accuracy and reducing modeling calculation time.

For example, there are scenarios in which a user requires to include both air and a mixed specie (Mix1) comprising the individual species nitrogen, oxygen, argon, and carbon dioxide. To accurately model the process, the simulation needs to be performed only on unique components components, and not on duplicated components, whether explicit (nitrogen-air, nitrogen-Mix1, oxygen-air, oxygen-Mix1, etc.) or implicit (treating air as a 'pure' specie, and Mix1 as a 'pure' specie, by using approximated composite properties). Instead, at least all thermodynamic calculations need to be done on unique species—all nitrogen as one component, all oxygen as one component, etc. The embodiments disclosed herein, having at least three layers, solve this problem.

Multiple Proprietary Mixed Species

Various preferred embodiments provide the ability to use multiple proprietary mixed species. It is critical for the accuracy and efficient computer operation contemplated by the invention that multiple proprietary mixed species may be used in a chemical process being modeled.

In various scenarios, a user is modeling a chemical process using multiple proprietary mixtures. For example, a sour gas sweetening process using two (or more) proprietary amine solvents needs to modeled. The amine solvents are different, but naturally have overlapping components—an individual specie like methyldiethanolamine (MDEA).

In some embodiments, nested mixed species—whether proprietary or not—are provided for. For example, a user may add a mixed specie representing Source A, and then define Source A as comprising various hydrocarbons, a pre-defined mixed specie of "salt water," etc. In various such embodiments, the mixed specie (e.g. Source A) is stored in the external layer, and its constituent species in the transformation object to the middle layer do not reference "Source A," but the various individual species of Source A. In such embodiments, the nested mixed specie is, therefore, primarily useful for ease in initial data entry of sources and other custom mixed species, and the nested mixed species are not maintained.

In other embodiments, a link is maintained to the nested mixed specie(s) in the transformation object, such as by a notation to individual species that are from the nested mixed specie(s). For example, a pre-defined mixed specie of "salt water" is maintained in a data structure (such as a table(s)), and the transformation object from the external layer, which includes the same Source A of various hydrocarbons and "saltwater," to the middle layer comprises a nested loop that displays the mixed specie constituents as a nested list: Hydrocarbon1-SourceA, Hydrocarbon2-Source A, etc., and "saltwater"-Source A[H2O-"saltwater"-Source A, Salt1-"saltwater"-Source, Salt 2-"salt water"-Source A, etc.], etc.

In some similar embodiments, the transformation object does not display a nested list, but simply creates extra duplicated components, as necessary—e.g. Pentane-Source X-Nested Mixed Specie 1, Pentane-Source X-Nested Mixed Specie 2, Pentane-Source X-Individually Entered.

Encryption

In various preferred embodiments, files and data storage structures comprising proprietary mixed specie(s) compositions are encrypted. In some such embodiments, the dataset—whether an individual file(s), an individual table(s), or individual entry(ies) in one or more tables—are kept encrypted. In particular such embodiments, at least the middle layer, and in some embodiments, at least the middle and internal layers, are encrypted. The unit operation(s) decrypt the data, perform the calculations, and encrypt the resulting data assigned to the outgoing stream(s). Only the data permitted to be visible to the user, according to visibility rules, such as those discussed elsewhere herein, are displayed in a decrypted format.

In various embodiments: displayable data is stored in one or more decrypted tables or table entries; displayable data is decrypted as requested by the user, and at least composition-related data is checked against visibility rules, or some combination thereof.

Various encryption methods are well-known and will be readily applied by persons of ordinary skill in the art. Furthermore, known methods of protecting data from visibility to the user, whether in place of or in addition to encryption, are further contemplated in some embodiments, and are within the context of this disclosure.

Conclusion

The invention claimed has been herein disclosed sufficiently for persons skilled in the art to comprehend and practice. The various embodiments, examples, and illustrations disclosed herein, while representing the best and various alternative modes of carrying out the invention as currently contemplated by the inventors, are by no means limiting or exhaustive, but serve as an aid to comprehending the full nature and scope of the invention. Various other embodiments will become apparent which fall within the scope of this disclosure and claims.

TABLE 1

EXAMPLE PROCESSES AND CALCULATIONS BENEFITING FROM IMPROVED COMPOSITION TRACKING ("Mixed Species")

| Process/Calculation | Benefits |
|---|---|
| Amine Treating | Mixed species allows use of proprietary blends of known amines, which can be modeled accurately with previously developed models, without divulging the blend composition to the end user. |
| Glycol Dehydration | Mixed species allows use of proprietary blends of known glycols, which can be modeled accurately with previously developed models, without divulging the blend composition to the end user. |
| Refining | Refineries often have multiple crudes blended in their feed stream. Mixed species allows for calculating the portion of the individual feeds in each of the product streams without duplicating components, which can cause inaccurate calculations in refinery process models. |
| Pipeline Transportation | Pipeline compression power requirements are dependent on calculating entropy correctly. Mixed species allow for accurate entropy calculation. |
| Well-Gathering | Mixed species preserves accuracy while tracking the source of components in a well-gathering network by avoiding duplication of components. |
| Gas Separation | A typical gas separation facility combines gas from multiple wells. Mixed species allows accurate calculation of individual feed portions in each of the product streams, avoiding inaccuracy from duplicated components. |
| Heat Transfer Fluid | Mixed species allows use of proprietary blends of known heat transfer fluids, which can be modeled accurately with previously developed models, without divulging the blend composition to the end user. |
| Mixed Refrigerants | Mixed species allows use of proprietary blends of known refrigerants, which can be modeled accurately with previously developed models, without divulging the blend composition to the end user. |
| Refrigeration | In many processes, the refrigerant contains one or more components that are also present in the process fluid that is being cooled. Using a mixed species component for the refrigerant prevents duplication of components in the simulation, thereby providing for faster solve times. |
| Cryogenic Separation | In cryogenic separation, the refrigerant often contains one or more components that are also present in the process fluid that is being cooled. Using a mixed species component for the refrigerant prevents duplication of components in the simulation, which can lead to slower solve times. |
| HVAC | HVAC is a subset of refrigeration, and inherits the same benefits. |
| Potential Component Duplication | In all cases where component duplication is avoided, solve times will be faster. In many cases, accuracy is improved. |

TABLE 2

EXAMPLE POTENTIAL INACCURACIES RESULTING FROM DUPLICATING COMPONENTS IN SELECTED PROCESS CALCULATIONS

| Calculation Type | Example Affected Unit Operations (or portions thereof) | Example Errors (SAFETY = potential safety issue) |
|---|---|---|
| Entropy (non-linear mixing rules) | Compressors | Incorrect power<br>Incorrect outlet temperatures<br>Incorrect efficiencies |
| | Expanders | Incorrect power<br>Incorrect outlet temperatures<br>Incorrect efficiencies |
| | Tank De-pressurization | Incorrect relief valve sizing<br>Incorrect tank temperatures (SAFETY) |
| | Tank Filling | Incorrect fill mass<br>Incorrect fill time<br>Incorrect pressure (SAFETY)<br>Incorrect temperature (SAFETY) |
| Gibbs Energy Reactions (depends on Depends on Entropy) | | Incorrect reaction equilibria |
| | Mixing | Incorrect phase equilibria |

TABLE 3

EXAMPLE CALCULATIONS AND METHODS USED HEREIN, AND EXAMPLE SOURCES THEREOF

| Type | Method/Calculation | Source(s) |
|---|---|---|
| Compressor & Expander Methods | Entropy mixing rules (compressor & expander methods depend on entropy mixing rules) | Thermodynamics textbooks, such as:<br>Smith, J. M., Van Ness, H. C., Abbott, M. M., Swihart, M. T. *Introduction to Chemical Engineering Thermodynamics.* Eighth edition. McGraw-Hill Education. ISBN 1259696529. |
| Flash Methods | Flash methods & calculations | Rachford, H. H., Jr.; Rice, J. D. Procedure for use of electronic digital computers in calculating flash vaporization hydrocarbon equilibrium JPT, J. Pet. Technol. 1952, 4, 327-328DOI: 10.2118/952327-G<br>Boston, J.; Britt, H. A radically different formulation and solution of the single-stage flash problem Comput. Chem. Eng. 1978, 2, 109- 122DOI: 10.1016/0098-1354(78)80015-5 |
| Equations of State | BWRS | Starling, K. E., Fluid Thermodynamic Properties for Light Petroleum Systems, Gulf Publishing Company, 1973. |
| | Chao-Seader | Chao, K. C. and J. D. Sender, "A Generalized Correlation of Vapor-Liquid Equilibria in Hydrocarbon Mixtures", AIChE Journal, 7 (4), 1961, pp. 598-605. |
| | EOS-CG (Equation of State for Combustion Gases) | Gernert, J., and R. Span, "EOS-CG: A Helmholtz energy mixture model for humid gases and CCS mixtures", J. Chem. Thermodynamics, 93, February 2016, pp. 274-293.<br>Span, R., and W. Wagner, "A New Equation of State for Carbon Dioxide Covering the Fluid Region from the Triple-Point Temperature to 1100 K at Pressures up to 800 MPa", J. Phys. Chem. Ref. Data, 25 (6), 1996, pp. 1509-1596.<br>Wagner, W., and A. Pruss, "The IAPWS Formulation 1995 for the Thermodynamic Properties of Ordinary Water Substance for General and Scientific Use", J. Phys. Chem. Ref. Data, 31 (2), 2002, pp. 387-535.<br>Span, R., E. W. Lemmon, R. T. Jacobsen, W. Wagner, and A. Yokozeki, "A Reference Equation of State for the Thermodynamic Properties of Nitrogen for Temperatures from 63.151 to 1000 K and Pressures to 2200 MPa", J. Phys. Chem. Ref. Data, 29 (6), 2000, pp. 1361-1433.<br>Schmidt, R., and W. Wagner, "A New form of the Equation of State for Pure Substances and its Application to Oxygen", Fluid Phase Equilibria, 19, 1985, pp. 175-200.<br>Tegeler, Ch., R. Span, and W. Wagner, "A New Equation of State for Argon Covering the Fluid Region for Temperatures from the Melting Line to 700 K at Pressures up to 1000 MPa", J. Phys. Chem. Ref. Data, 28(3), 1999, pp. 779-850.<br>Lemmon, E. W., and R. Span, "Short Fundamental Equations of State for 20 Industrial Fluids", J. Chem. Eng. Data, 51, 2006, pp. 785-850. |

TABLE 3-continued

EXAMPLE CALCULATIONS AND METHODS USED
HEREIN, AND EXAMPLE SOURCES THEREOF

| Type | Method/Calculation | Source(s) |
|---|---|---|
| | GERG-2008 | Kunz, O. and W. Wagner, "The GERG-2008 Wide-Range Equation of State for Natural Gases and Other Mixtures: An Expansion of GERG-2004", J. Chem. Eng. Data, 57 (11), 2012, pp. 3032-3091. Kunz, O., R. Klimeck, W. Wagner, and M. Jaeschke, "The GERG-2004 Wide-Range Equation of State for Natural Gases and Other Mixtures", GERG Technical Monograph 15, Groupe Européen de Recherches Gazières, 2007, pp. 1-555. |
| | HOC | Prausnitz, J. M., T. F. Anderson, E. A Grens, C. A. Eckert, R. Hsieh, and J. P. O'Connell, Computer Calculations for Multicomponent Vapor-Liquid and Liquid-Liquid Equilibria (Prentice-Hall International Series in the Physical and Chemical Engineering Sciences), Prentice-Hall, 1980. |
| | Lee-Kesler | Lee, B. I. and M. G. Kesler, "A Generalized Thermodynamic Correlation Based on Three-Parameter Corresponding States," AIChE Journal, Vol. 21, No. 3, May, 1975, pp. 510-527. |
| | Peng-Robinson | Reid, R. C., J. M. Prausnitz, and B. E. Poling, The Properties of Gases and Liquids, 4th ed., McGraw-Hill Book Company, 1987. |
| | SAFT-VR | Gil-Villegas, A., A. Galindo, P. J. Whitehead, S. J. Mills, G. Jackson, and A. N. Burgess, "Statistical associating fluid theory for chain molecules with attractive potentials of variable range," J. Chem. Phys., 106 (10), Mar. 8, 1997, p. 4168. Galindo, A., L. A. Davies, A. Gil-Villegas, and G. Jackson, "The thermodynamics of mixtures and the corresponding mixing rules in the SAFT-VR approach for potentials of variable range," Mol. Phys., Vol. 93, No. 2, 1998, pp. 241-252. Huang, S. H., and M. Radosz, "Equation of State for Small, Large, Polydisperse, and Associating Molecules," Ind. Eng. Chem. Res., 29, 1990, pp. 2284-2294. BRE-MXSP-P201909 |
| | SRK | Reid, R. C., J. M. Prausnitz, and T. K. Sherwood, The Properties of Gases and Liquids, 3rd ed., McGraw-Hill Book Company, 1977 |

We claim:

1. A system for modeling of chemical processes comprising:
    (1) a computer system comprising a data processing unit, and having access to at least one data storage device; and
    (2) computer code in said computer system, said computer code comprising:
        (a) means for evaluating chemical process models; each process model comprising one or more unit operations, one or more input streams into each unit operation, and one or more output streams from each unit operation; each of the streams comprising chemical composition data; each of the unit operations comprising one or more calculations transforming data from at least one of the streams connected thereto and accordingly updating data of at least one of the streams connected thereto;
        (b) at least three layers: an external layer, a middle layer, and an internal layer; the external layer comprises mixed species, individual species, or both, as determined by a user; the middle layer comprises individual species duplicated by source; and the internal layer comprises only unique individual species;
        (c) transformation objects to convert between the three layers;
        (d) component-sensitive calculation rules directing each unit operation, or portion thereof, to operate on either the middle layer or internal layer; and
        (e) calculation efficiency rules directing each unit operation, or portion thereof, to operate on either the middle layer or internal layer.

2. The system of claim 1 wherein at least one of the input streams of (2)(a) is a mixed species stream representing at least one mixed specie, and there is included proportions data of the individual species comprising the at least one mixed specie.

3. The system of claim 1 adapted for use with proprietary mixed species, wherein the computer code further comprises visibility rules prohibiting unauthorized users from viewing the composition of proprietary mixed species, said rules including activating transformation objects when users view data from the middle layer or internal layer to present to the user only the external layer for proprietary mixed species.

4. The system of claim 1, wherein the component-sensitive calculations rules comprise one or more rules directing thermodynamic calculations to be performed on the internal layer.

5. The system of claim 1, wherein the unit operations comprise thermodynamic operations.

6. The system of claim 1, wherein the unit operations comprise at least one entropy operations, and Gibbs free energy operations.

7. The system of claim 1, wherein the unit operations further comprise allocation.

8. A method for improving the operation of at least one computer during chemical process modeling, the method comprising:
(a) evaluating a chemical process model; the process model comprising one or more unit operations, one or more input streams into each unit operation, and one or more output streams from each unit operation; each of the streams comprising chemical composition data; each of the unit operations comprising one or more calculations transforming data from at least one of the streams connected thereto and accordingly updating data of at least one of the streams connected thereto;
(b) maintaining stream composition data in at least three layers: an external layer, a middle layer, and an internal layer; the external layer comprises mixed species, individual species, or both, as determined by a user; the middle layer comprises individual species duplicated by source; and the internal layer comprises only unique individual species;
(c) applying component-sensitive calculation rules to direct each unit operation, or portion thereof, to operate on either the middle layer or internal layer;
(d) applying calculation efficiency rules directing each unit operation, or portion thereof, to operate on either the middle layer or internal layer; and
(e) applying transformation objects to convert between the three layers as directed by rules, including the component-sensitive calculation rules and the calculation efficiency rules.

9. The method of claim 8 wherein at least one of the input streams of (4)(a) is a mixed species stream representing at least one mixed specie, and there is included proportions data of the individual species comprising the at least one mixed specie.

10. The method of claim 8 adapted for use with proprietary mixed species, further comprising visibility rules prohibiting unauthorized users from viewing the composition of proprietary mixed species, said rules including activating transformation objects when users view data from the middle layer or internal layer to present to the user only the external layer for proprietary mixed species.

11. The method of claim 8, wherein the component-sensitive calculations rules comprise one or more rules directing thermodynamic calculations to be performed on the internal layer.

12. The method of claim 8, wherein the unit operations comprise thermodynamic operations.

13. The method of claim 8, wherein the unit operations further comprise at least one of: entropy operations, and Gibbs free energy operations.

14. The method of claim 8, wherein the unit operations further comprise allocation.

15. At least one non-transitory computer readable medium containing program instructions for causing a computer to perform a method for improving the operation of at least one computer during chemical process modeling, the method comprising:
(a) evaluating a chemical process model; the process model comprising one or more unit operations, one or more input streams into each unit operation, and one or more output streams from each unit operation; each of the streams comprising chemical composition data; each of the unit operations comprising one or more calculations transforming data from at least one of the streams connected thereto and accordingly updating data of at least one of the streams connected thereto;
(b) maintaining stream composition data in at least three layers: an external layer, a middle layer, and an internal layer; the external layer comprises mixed species, individual species, or both, as determined by a user; the middle layer comprises individual species duplicated by source; and the internal layer comprises only unique individual species;
(c) applying component-sensitive calculation rules to direct each unit operation, or portion thereof, to operate on either the middle layer or internal layer;
(d) applying calculation efficiency rules directing each unit operation, or portion thereof, to operate on either the middle layer or internal layer; and
(e) applying transformation objects to convert between the three layers as directed by rules, including the component-sensitive calculation rules and the calculation efficiency rules.

16. The at least one non-transitory computer readable medium containing program instructions of claim 15 wherein at least one of the input streams of (7)(a) is a mixed species stream representing at least one mixed specie, and there is included proportions data of the individual species comprising the at least one mixed specie.

17. The at least one non-transitory computer readable medium containing program instructions of claim 15 adapted for use with proprietary mixed species, further comprising visibility rules prohibiting unauthorized users from viewing the composition of proprietary mixed species, said rules including activating transformation objects when users view data from the middle layer or internal layer to present to the user only the external layer for proprietary mixed species.

18. The at least one non-transitory computer readable medium containing program instructions of claim 15, wherein the component-sensitive calculations rules comprise one or more rules directing thermodynamic calculations to be performed on the internal layer.

19. The at least one non-transitory computer readable medium containing program instructions of claim 15, wherein the unit operations comprise at least one of: thermodynamic operations, entropy operations, and Gibbs free energy operations.

20. The at least one non-transitory computer readable medium containing program instructions of claim 15, wherein the unit operations further comprise allocation.

* * * * *